(12) United States Patent
Davies et al.

(10) Patent No.: US 11,944,795 B2
(45) Date of Patent: Apr. 2, 2024

(54) INJECTION DEVICE WITH SAFE TRIGGER FUNCTION

(71) Applicant: Owen Mumford Limited, Woodstock (GB)

(72) Inventors: Callum Davies, Woodstock (GB); Abiodun Falodi, Woodstock (GB); Matthew Farmer, Woodstock (GB); Oliver Gould, Woodstock (GB); Oliver Hyde, Woodstock (GB); Parshia Moghadas, Woodstock (GB); Timothy Muller, Woodstock (GB); Tahir Shabudin, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 194 days.

(21) Appl. No.: 17/374,003

(22) Filed: Jul. 13, 2021

(65) Prior Publication Data
US 2021/0338937 A1  Nov. 4, 2021

Related U.S. Application Data

(62) Division of application No. 15/570,700, filed as application No. PCT/EP2016/059692 on Apr. 29, 2016, now Pat. No. 11,097,059.

(30) Foreign Application Priority Data

Apr. 30, 2015 (GB) ..................... 1507498

(51) Int. Cl.
*A61M 5/315* (2006.01)
*A61M 5/20* (2006.01)
(Continued)

(52) U.S. Cl.
CPC ...... *A61M 5/31513* (2013.01); *A61M 5/2033* (2013.01); *A61M 5/31511* (2013.01);
(Continued)

(58) Field of Classification Search
CPC ............ A61M 5/31513; A61M 5/2033; A61M 5/31511; A61M 5/3202; A61M 5/326;
(Continued)

(56) References Cited

U.S. PATENT DOCUMENTS 7,419,478 B1 * 9/2008 Reilly ............... A61M 5/14546
604/218
2005/0277885 A1 12/2005 Scherer
(Continued)

FOREIGN PATENT DOCUMENTS

GB         2414398 A    11/2005
WO   WO2009040602 A1    4/2009
(Continued)

OTHER PUBLICATIONS

Search Report for GB Application No. 1507489.2 dated Nov. 5, 2015, 5 pages.
(Continued)

*Primary Examiner* — Phillip A Gray
(74) *Attorney, Agent, or Firm* — Quarles & Brady LLP

(57) ABSTRACT

An injection device is disclosed comprising a plunger for expressing medicament from a syringe and a delivery mechanism arranged in use to provide a forward biasing force to urge the plunger from a first rearward position to a second forward position to express a dose from the syringe. A latch arrangement is provided that releasably holds the plunger against the force of the delivery mechanism. The latch arrangement comprising at least two resilient segments which define opposing sections of an aperture within which a rearward end of the plunger is retained in the rearward
(Continued)

position. A trigger is provided for releasing the plunger in use, the trigger being arranged to outwardly deflect at least one of the resilient segments such that the aperture is expanded to release the rearward end of the plunger. A method of manufacturing the injection device is also enclosed.

7 Claims, 13 Drawing Sheets

(51) Int. Cl.
 *A61M 5/32* (2006.01)
 *A61M 5/24* (2006.01)
(52) U.S. Cl.
 CPC .......... *A61M 5/3202* (2013.01); *A61M 5/326* (2013.01); *A61M 2005/2073* (2013.01); *A61M 5/24* (2013.01); *A61M 2005/31508* (2013.01); *A61M 2005/31521* (2013.01); *A61M 2207/00* (2013.01); *A61M 2207/10* (2013.01)
(58) Field of Classification Search
 CPC ............ A61M 5/24; A61M 2005/2073; A61M 2005/31508; A61M 2005/31521
 USPC ....................................................... 604/228
 See application file for complete search history.

(56) References Cited

U.S. PATENT DOCUMENTS

| | | | |
|---|---|---|---|
| 2009/0312705 A1* | 12/2009 | Grunhut | ............... A61M 5/326 604/110 |
| 2013/0324934 A1 | 12/2013 | Holmqvist et al. | |
| 2014/0135705 A1 | 5/2014 | Hourmand et al. | |

FOREIGN PATENT DOCUMENTS

| | | |
|---|---|---|
| WO | WO2009092807 A1 | 7/2009 |
| WO | WO2009114542 A1 | 9/2009 |
| WO | WO2011109205 A2 | 9/2011 |
| WO | WO2012085585 A2 | 6/2012 |
| WO | WO2014062488 A1 | 4/2014 |
| WO | WO2014140820 A2 | 9/2014 |
| WO | WO2015011488 A1 | 1/2015 |

OTHER PUBLICATIONS

International Search Report and Written Opinion for PCT Application No. PCT/EP2016/059692, dated Oct. 17, 2016, 23 pages.

\* cited by examiner

INJECTION DEVICE WITH SAFE TRIGGER FUNCTION

CROSS-REFERENCE TO RELATED APPLICATIONS

This application is a divisional of U.S. application Ser. No. 15/570,700, filed on Oct. 30, 2017, which is the U.S. National Stage of International Application No. PCT/EP2016/059692 filed on Apr. 29, 2016, which is incorporated by reference in its entirety, and is based upon, claims priority to, and incorporates herein by reference in its entirety, United Kingdom Patent Application Serial No. GB 1507498.2, filed Apr. 30, 2015.

FIELD OF THE INVENTION

The invention relates to injection devices for delivering a dose of medicament from a syringe. In particular, but not exclusively, embodiments of the invention relate to a trigger arrangement for an injection device.

BACKGROUND OF THE INVENTION

Injection devices are used for the convenient administration of medicaments. For example, injection devices (which may typically be in the form of a pen injector) may be used for providing a single metered dose of a medicament, such as Epinephrine, in an emergency or for providing regular metered doses of a medicament, such as Insulin. Such devices may be either single use "disposable" devices in which the device is typically provided with a syringe already installed, and which is not user-replaceable, or "reusable" devices which allow the user to replace the syringe when the medicament has been used.

It may be noted that whilst the term "syringe" is used herein for clarity and convenience, the skilled person will appreciate that in some arrangements the syringe may be a cartridge (which, for example, may be arranged to receive a disposable needle). In some arrangements the syringe/cartridge may formed integrally with the (or part of the) injection device.

Injection devices may be provided in the form of an "autoinjector" device. As used herein an autoinjector is an injector device in which, in addition to automating the delivery of the medicament, the device is also arranged to automate the insertion of a needle into the skin prior to the delivery of the medicament.

Injection devices generally comprise a delivery mechanism which is arranged to automatically deliver a dose from the syringe, and optionally (particularly in the case of an autoinjector) to first displace the syringe, which may be held in a syringe carrier, within the housing to cause needle penetration. The delivery mechanism may typically be released from an energised (or primed) position and may, for example, include one or more drive springs. The delivery mechanism may act upon a plunger which includes or acts against a piston (also referred to as a "bung") which is slidably provided within the syringe. In the case of an autoinjector the initial stiction between the piston and syringe may resist forward movement of the piston relative to the syringe such that initially the delivery mechanism moves the syringe (and syringe carrier) into the needle insertion position (whereupon further movement of the syringe is blocked and the delivery mechanism will continue to move forward thus moving the piston).

A trigger, for example in the form of a button on the end of the device, is generally provided to allow the user to activate the delivery sequence. In some injectors the trigger may alternatively be provided by an arrangement which automatically activates the delivery sequence in response to a forward end of the device being pressed against an injection site. It is also known to provide a safety arrangement in the form of a mechanical lock (which is referred to herein as an "interlock") arranged to prevent actuation of the delivery mechanism by the user unless the lock is in the unlocked position. For example, such safety arrangements may require the user to perform a readying action prior to releasing the trigger or may be arranged to require the injection device to be in contact with an injection site before the trigger is able to activate the delivery mechanism.

An injector device has been proposed in the applicant's co-pending Published International Patent Application No. WO2015/011488. This injector provides an arrangement in which an enlarged head (relative to at least a forward neck portion) at the rearward end of the plunger is initially held by a latch against the force of a drive spring. The latch includes an aperture which radially expands to allow the plunger to be released. A further injection device which operates using a similar principle is also disclosed in the applicant's co-pending International Patent Application WO2016/051168 (claiming priority from GB1417285.2).

SUMMARY OF THE INVENTION

According to a first aspect of the invention there is an injection device comprising: a plunger for expressing medicament from a syringe; a delivery mechanism arranged in use to provide a forward biasing force to urge the plunger from a first rearward position to a second forward position to express a dose from the syringe; a latch arrangement arranged to releasably hold the plunger against the force of the delivery mechanism, the latch arrangement comprising at least two resilient segments which define opposing sections of an aperture within which a rearward end of the plunger is retained in the rearward position; and a trigger for releasing the plunger in use, the trigger being arranged to outwardly deflect at least one of the resilient segments such that the aperture is expanded to release the rearward end of the plunger; and wherein the plunger comprises: a reduced cross section neck configured to be received in the aperture of the latch and a head rearwardly of the neck to retain the plunger when the latch is in its non-deflected position; and wherein a forward facing transition surface extends from the neck to the head, the transition surface having an asymmetric profile. For example the cross sectional profile may be asymmetric.

Advantageously the provision of an asymmetric profile to the head/neck of the plunger may reduce the risk that the plunger can, on its own overcome the resilient sections of the latch members apart (and may therefore decrease the risk of unintended release of the plunger). In particular the asymmetric profile may prevent the plunger head from urging the opposing sides of the latch members radially outwardly.

The forward facing transition surface may comprise segments having different profiles. For example the forward facing transition surface may comprises a first segment having a first forward incline angle and a second segment having a reduced forward incline angle. The second segment, having a reduced forward incline angle, could have a zero or negative (i.e. rearward) angle of forward incline. The second segment may have a shallow forward angled profile.

The first and second segments may extend through opposing radial sides of the plunger. The segments may each engage a different resilient segment of the latch.

The forward facing surface of the second segment may extend substantially radially. Thus, the second segment may provide a substantially transverse surface which extends perpendicular to the axis of the plunger. The second segment may therefore provide a substantially flat engagement face with the corresponding rearward face of the latch. The provision of a substantially flat engagement face between the latch and the plunger head may ensure that if the surfaces are urged together (for example when the device is dropped or subjected to a jarring force) the latch surfaces are, at least, not urged apart by the plunger and may be urged together. Thus the substantially flat surface may help to prevent unintended release.

The skilled person will appreciate that functionally a substantially flat engagement face may include a slight forward or rearward incline provided it prevented unintended release and did not prevent release when correctly triggered.

The plunger and the latch may further be provided with complimentary non-rotational features. The non-rotational features prevent relative rotation thereof. The complimentary non-rotational features may for example comprise a keyed engagement between the neck and the aperture. In devices including an injection indication device (for example an audible or tactile "injection complete" indicator) the non-rotational features may help ensure correct operation of the indication device.

The trigger may further comprise an alignment member to maintain the correct alignment of the plunger during activation. Such a feature may for example be provided on an interior surface of the trigger. The feature may abut or engage the rearward end of the plunger to prevent the plunger from not releasing when the latch is deflected. This may for example reduce the risk of the plunger catching on the latch and not releasing as intended.

According to a further aspect of the invention there is provided injection device comprising: a plunger for expressing medicament from a syringe; a delivery mechanism arranged in use to provide a forward biasing force to urge the plunger from a first rearward position to a second forward position to express a dose from the syringe; a latch arrangement arranged to releasably hold the plunger against the force of the delivery mechanism, the latch arrangement comprising at least two resilient segments which define opposing sections of an aperture within which a rearward end of the plunger (which may include an enlarged head) is retained in the rearward position; and a trigger forwardly moveable relative to the latch arrangement in use to release the plunger from the latch member, wherein the trigger and resilient segments of the latch member are provided with complementary camming surfaces configured to engage when the trigger is moved and to outwardly deflect at least one of the resilient segments in response to the (forward) movement of the trigger such that the aperture is expanded to release the end of the plunger. The trigger may include at least one side wall extending into the injection device adjacent to a side wall of the latch arrangement. The side walls of the trigger may and the latch may include the complementary camming surfaces The opposing sections may be opposing sides or quadrants of the latch member. The opposing sides or quadrants being urged apart by the camming action. The outward deflection of the resilient segments may be transverse relative to the longitudinal axis of the injection device, for example in a generally radially outward direction.

Advantageously, the arrangement of embodiments of the invention may provide an arrangement in which the release movement of the latch during actuation may be precisely controlled and/or predetermined. It will be appreciated that the latch and release arrangement must balance the conflicting requirements of avoiding accidental or premature release whilst also providing an arrangement which can be easily activated by an end user (which could for example include the elderly or frail). Thus, embodiments may provide a particularly reliable release mechanism. Embodiments could, for example, be useful in arrangements using relatively high force springs (for example due to high viscosity drugs or small needle diameters) where the latch hold may be required to be stronger.

One of the camming surfaces may comprise a forwardly inward sloped surface. The other of the camming surfaces may comprise a ridge or protrusion. The ridge may be generally axially extending. The sloped surface may be formed on the latch. The sloped surface may be formed by an outwardly extending surface.

The complementary camming surfaces may comprise a pair of spaced apart complementary camming surfaces. The pair of camming surfaces may be arranged to deflect the resilient segments outwardly away from one another.

The camming surface of the trigger may be provided on an inner surface of a side wall of the trigger. The side wall may generally extend forwardly in the axial direction. The side wall may be radially outside of the latch (and may be between an outer housing and the latch). The side wall may extend forwardly from a rearward portion of the trigger. At least in its forward position, the side wall may partially surround the latch. The rearward portion of the trigger may include a transverse wall. The rearward portion may close the rearward end of the device. The rearward portion may be arranged to be engaged by the user (and may define a rearward user engagable button). For example, the user may press the rearward portion forward (for example with the thumb) during use.

The camming surface of the trigger may comprise at least one inward protrusion from the side wall. The surface may be an axially extending rib extending forwardly along a length of the side wall (and, for example, arranged to move into contact with the corresponding camming surface of the latch upon forward movement of the trigger). The aperture, within which an enlarged head of a rearward end of the plunger is retained, may be formed in a transverse rearward wall of the latch arrangement. The camming surface of the latch arrangement may be provided on an outer sidewall of the resilient segments of the latch member. The side wall may generally extend forwardly in the axial direction from the transverse wall. The side wall may be radially inside the side wall of the trigger (at least when the trigger is moved forwardly towards the activation position).

The side walls of the trigger and the latch may be at least partially concentric. The side wall of the latch may extend internally within the housing of the injection device. The side wall of the latch may be generally annular. The side wall of the trigger may be generally annular. The side walls of the trigger and the latch may be substantially parallel. The side walls of the trigger and the latch may each extend along a longitudinal direction of the injection device (which it will be appreciated may generally be parallel to the axis of the needle associated with the syringe). The trigger may move forwardly in use relative to the latch in the longitudinal direction. Thus, during use the side wall of the trigger may move in a direction which is parallel to the side wall of the latch. Thus the complementary camming surfaces of the trigger and the latch member may slidingly engage in the longitudinal direction.

The camming surfaces of the latch may comprise a camming surface on each of the resilient segments.

The trigger may generally radially surround the latch member (at least when the trigger is in a forward position). The trigger and resilient segments of the latch member may be provided with a plurality of sets of complementary camming surfaces at spaced apart locations. For example, first and second sets of complementary camming surfaces may be provided at opposing sides of the injection device. The latch may be segmented into quadrants. In such an arrangement, a set of complementary camming surfaces on each side of the device may respectively each be arranged to urge two of the quadrants outwardly away from one another.

The trigger may comprise an axially moveable button disposed at the rear of the injector. Thus, the trigger may be movable relative to the housing to provide relative movement to the latch.

The injection device may comprise a front housing and a rear housing. The front housing and rear housing may be slidably connected. In some embodiments the front housing and rear housing may be configured to slide relative to one another as an initiation or interlock arrangement prior to a moveable trigger button being activated. In alternate embodiments the rear housing may comprise the trigger. The trigger may, therefore, be fixed relative to the rear housing (such that sliding movement between the front and rear housing itself provides the activation movement).

The forward movement of the rear housing relative to the front housing may disengage an interlock arrangement which blocks the forward movement of the trigger relative to the latch arrangement.

The rear housing may further comprise a blocking arrangement which restricts expansion of the latch. The blocking arrangement may directly restrict or block the expansion of the latch. For example, the blocking arrangement comprises ribs which prevent movement of the camming surfaces of the latch. Advantageously by blocking movement of the camming surfaces embodiments of the invention may provide an arrangement in which the components will lock or "bind" together in the event that the mechanism is operated in an incorrect sequence (or accidentally jarred/dropped). For example, the camming surfaces of the latch may become jammed between the blocking arrangement and the camming surfaces of the trigger.

The blocking arrangement may be formed by, or provided on, an inner surface of the rear housing. The rear housing may for example be provide with a substantially annular flange extending inwardly from its interior surface and wherein the blocking arrangement extents from the flange. The flange may form part of the interlock arrangement which prevents movement of the trigger prior to forward movement of the rear housing.

The choice of whether the device is activated by a two-step motion, requiring the user to press the injector against the injection site to provide relative axial movement between the housing portions in addition to the pressing of a trigger button, or a single step motion, in which the actuation is automatic in response to the device being pressed against an injection site to provide relative axial movement between the housing portions, may depend upon the intended use of the device (for example to particular medicament to be delivered). As such, it will be appreciated that both arrangements may be useful.

Accordingly, in a further aspect the present invention provides a method of modular manufacture of an injector device comprising: providing a common forward body assembly; providing a common delivery mechanism assembly; providing two alternate rear body assemblies types wherein: a first rear body assembly type is provided with a trigger moveable relative to a rear housing and a second rear body assembly type is provided with a trigger fixed relative to a rear body housing.

Also a further aspect of the invention may provide a modular manufacturing system for injection devices having different modes of actuation, the injection devices comprising: a forward assembly; a delivery mechanism; and a rear body assembly, the rear body assembly being provided with two alternate arrangements: a first rear assembly type for providing a button activated injection device, the first rear assembly including a trigger button moveably mounted on a rear housing for activating the delivery mechanism in use; and a second rear assembly type for providing a pressure activated injection device, the second rear assembly including a trigger for activating the delivery mechanism, the trigger being fixed relative to the rear housing and the rear housing being slidably attached to the forward assembly.

Advantageously, the method/system of the invention may provide an increased commonality between the two types of device to simplify and reduce the cost of manufacturing. A substantially similar forward housing assembly and delivery mechanism may be used for both types of device.

The front assembly may for example include one or more of the following components: a forward housing, a syringe of medicament, a needle, a cap, a syringe carrier and a deployable needle shroud. The delivery mechanism may include one or more of the following components a plunger, a drive spring, a latch mechanism, a dose setting arrangement and an injection completion indicator. Thus, it will be readily appreciated that the part count of the rear assembly (which is the unique part between the two different versions of the device) may be minimal. For example, the rear body assembly may comprise a rear housing and may include a trigger (which may optionally be a moveable button provided with a trigger biasing spring).

The delivery mechanism may be fixed relative to the forward assembly. Conveniently the front body assembly may be provided with a syringe of medicament which is then secured therein by attaching the delivery mechanism. Thus, a sub assembly may be provided including all of the common injection device features prior to assembly with a rear body assembly of the required type.

The rear body assembly may be arranged to be slidably connected to the forward body assembly. This may be the case for both injection device types since the moveable trigger version may use a sliding rear housing to provide an interlock or initiation arrangement.

The second rear assembly type may comprise a trigger member which is fixed relative to a rear housing. The trigger member may be a fixed element provided in place of a trigger button. The rear assembly may include a closure which closes an aperture in the rear housing (which would otherwise be provided with a moveable trigger button). The closure may comprise the trigger member (for example the closure may include a trigger feature such as a protrusion for engaging the latch of the delivery mechanism in use). The closure or trigger member may snap fit into the rear housing. The trigger member may include a trigger.

The first rear assembly type may comprise a trigger member moveably attached to a rear housing. The trigger member may be slidably attached to the rear housing and may be biased rearwardly.

In an initial (pre-use) assembled arrangement the rear assembly may engages a latch mechanism of the delivery mechanism. For example, the rear assembly may resiliently engage the forward assembly or delivery mechanism (for example the latch mechanism) and may be arranged to disengage forwardly during actuation of the injection device. Once the trigger has moved forward relative to the latch, the rearward housing may re-engage the forward assembly or delivery mechanism in a second position (which may for example provide a visual indication that the device has been activated and/or to prevent an attempt to reuse the device). The rear body assembly may be provided with resilient members (for example sprung arms) to provide the engagement arrangement. In particular, the engagement may be arrangement between the trigger button or closure element and the forward assembly or delivery mechanism.

Whilst the invention has been described above, it extends to any inventive combination or sub-combination of novel features set out above, or in the following description or claims.

BRIEF DESCRIPTION OF THE DRAWINGS

The invention may be performed in various ways and an embodiment thereof, with various modifications, will now be described by way of example only, reference being made to the accompanying drawings in which.

DETAILED DESCRIPTION OF EMBODIMENTS

Front as used herein will be understood to refer to the end of the injector assembly (or components thereof), in use, are closest to the delivery needle delivery end of the injector (i.e. the end which is pointed at the skin). Rear as used herein will be understood to refer to the end of the pen injector assembly (or components thereof) which, in use, are furthest from the needle delivery end of the injector (i.e. the end which is pointed away from the skin). Forward and rearward will, likewise, be understood to refer to the directions orientated towards the front and rear of the injector assembly.

Axial, radial and circumferential are used herein to conveniently refer to the general directions relative to the longitudinal direction of the injection device (or components thereof). The skilled person will, however, appreciated that these terms are intended to be broadly interpreted (and for example, the injection device may have a non-circular and/or irregular form). Typically, regardless of the chosen injector device external profile the cartridge or syringe will have a conventional generally cylindrical form and, as such, the longitudinal axis of the injection device will substantially coincide with (or be parallel to) the axial direction of the syringe.

Figure 1:
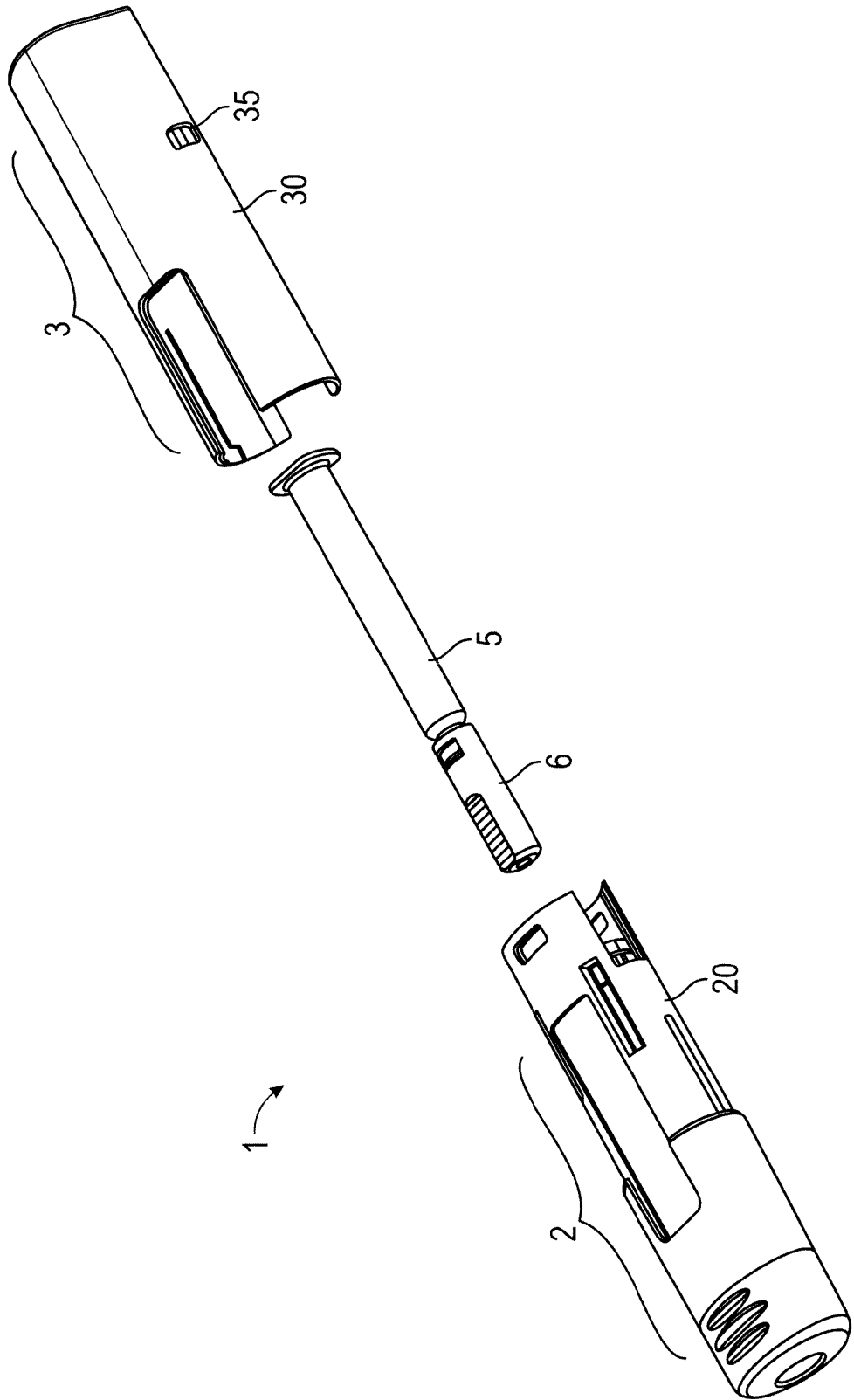
FIG. 1 is a partial exploded view of an auto injector according to an embodiment showing the syringe, forward assembly and rearward assembly.

As seen in FIG. 1, an autoinjector 1 in accordance with an embodiment of the invention comprises a housing defined by a forward housing 20 and a rearward housing 30. A syringe 5 of medicament is provided within the housing. The housing 20, 30 has a generally elongate tubular shape with a generally oval cross-sectional profile.

The syringe 5 is a conventional syringe having a bung or stopper 7 within its body and a needle at its forward end which may initially be protected (so as to remain sterile) by a removable needle shield 6. The illustrated autoinjector 1 is generally intended to be a single use device (although the skilled person will appreciate that the invention is not limited to such devices) and, therefore, the exploded view of FIG. 1 may typically represent a final assembly stage in which the syringe is placed into the housing (for example in a manufacturing facility). The end user would typically be provided with the autoinjector 1 preassembled around the syringe 5 (as for example, shown in FIG. 4). As will be explained in further detail below, the autoinjector may conveniently be arranged during manufacture into a forward assembly 2, a delivery mechanism 40, and a rearward assembly 3. The forward assembly 2 is formed around the forward body 20 and comprises those components which are initially forward of the syringe 5. The delivery mechanism 40 comprises the components for delivering medicament from the syringe. The rearward assembly 3 is formed around the rearward body 30 and comprises those components which are initially rearward of the syringe 5.

Figure 2:
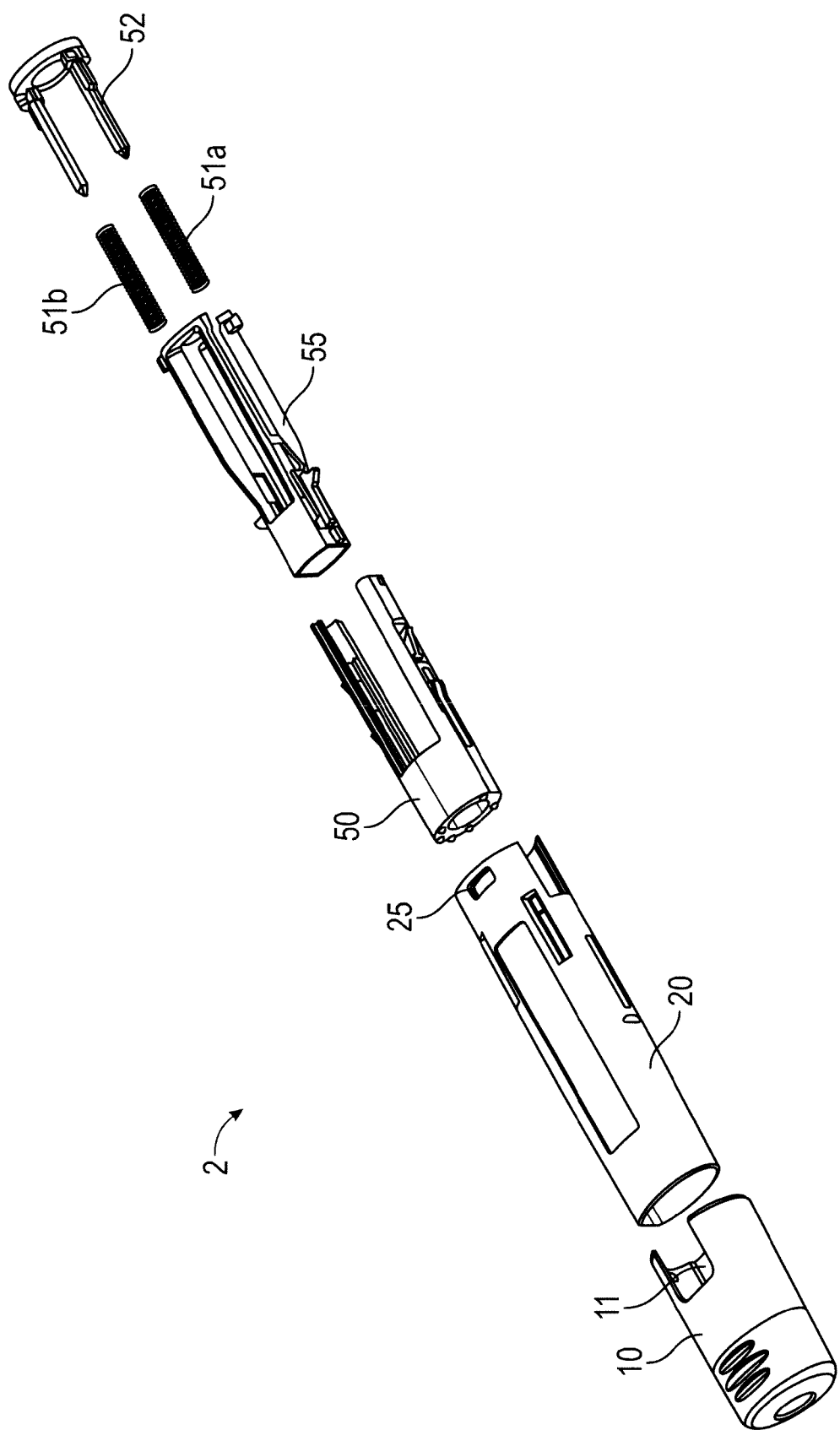
FIG. 2 is an exploded view of the forward sub-assembly of FIG. 1.
Figure 3:
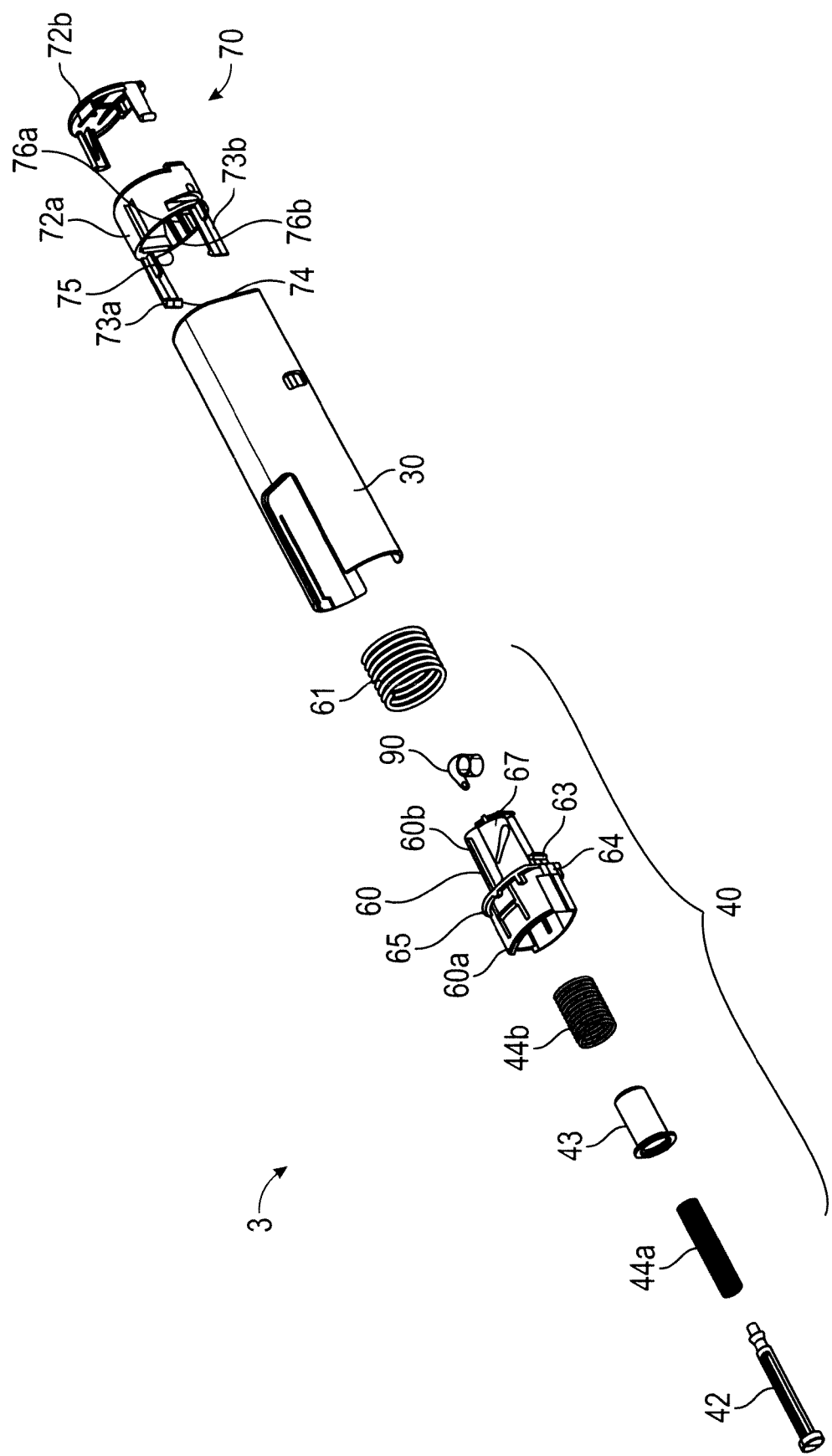
FIG. 3 is an exploded view of the rearward sub-assembly of FIG. 1.

An exploded view of each of the forward assembly is shown in FIG. 2 and the delivery mechanism and rearward sub-assemblies are shown in FIG. 3.

The forward assembly 2 comprises the forward body 20 which is adapted to receive a cap 10 which closes the forward end of the autoinjector 1. Within the assembly 2 there is a syringe carrier 55 for movably mounting the syringe within the forward body 20 to enable automatic needle penetration.

A needle shroud 50 is also provided and arranged to shroud the needle after use (when the syringe 5 and syringe carrier 55 are in a forward position) to prevent needle stick injuries. The shroud 50 is activated by a pair of side-by-side shroud springs 51a, 51b carried on a spring guide 52. The syringe carrier 55 and/or needle shroud 50 are not essential to the present invention and, as such, the operation of the shroud 50 and carrier 55 is not described in detail. However, it may be noted that the arrangement is generally of the type described in the applicants' earlier International Patent Application PCT/GB2011/052557.

The rear assembly 3 includes a trigger button 70 which is inserted into the rearward housing 30 from the rearward end so as to substantially close the rearward end of the injector housing. The trigger button 70 has a cup-like profile with side walls which are arranged to fit within (and be substantially concentric with) the rearward housing 30 and an end wall which closes the rear end of the housing. The trigger button 70 may conveniently comprise a single moulded part. However, for ease of manufacture and or assembly, in the embodiment of FIG. 3 the trigger button 70 includes a main body 72a and a rear cover 72b. Alternatively, the cover 72b may be overmoulded on the main body 72a (for example to provide a textured button surface). The main body 72a includes a pair of forwardly extending resilient arms 73a and 73b which are arranged to provide an engagement between the trigger button 70 and the injector 1.

The drive mechanism 40 is positioned between the front assembly 2 and rear assembly 3. The drive mechanism 40 includes a plunger 42 which is arranged to engage the bung of the syringe in use. The plunger 42 is driven forwards in use by a pair of concentric drive springs 44a and 44b (although it will be appreciated that in other embodiments a single spring may be used) with an intermediate drive member 43 provided therebetween. A latch 60 is arranged concentrically around the drive springs 44, intermediate member 43 and plunger 42. The latch 60 is arranged to hold the plunger 42 against the bias of the springs 44 until the latch is released via the trigger button 70 (when both drive springs and the intermediate drive member are all released together). The latch 60 comprises a rear body portion 60b having a split cylinder profile formed of four quadrants extending rearwardly from a forward connecting body portion 60a. As described in further detail below, each quadrant is resiliently deflectable in use from the initial position (shown in FIG. 3). The quadrants meet at a rear lateral surface of the latch 60b where they define a latch aperture 66 at its rear end for holding the rearward end 42a (which is at least locally radially enlarged) of the plunger 42. The forward body portion 60a has an external profile substantially corresponding to the interior profile of the rearward end of the forward housing 20. The basic functional operation of the drive mechanism 40 is substantially as described, for example, in the applicants' earlier International Patent Applications PCT/GB2011/051950 and PCT/GB2014/052276.

The rearward assembly also includes an indicator arrangement 90 provided by an elongate sprung member which is attached to the plunger 42.

A housing biasing spring 61 is provided within the rearward assembly 3 and in the assembled arrangement is captive between the latch 60 and rearward housing 30. Thus, the biasing spring 61 urges the forward and rearward sub-assemblies 2, 3 towards an initial expanded state.

The connection between the sub-assemblies 2, 3 is provided via the latch 60 which it acts as an intermediate connecting member. The interconnection is a resilient snap fit connection which provides for ease of manufacture particularly for a single-use device (which the user will not be required to disassemble). Thus, it may be noted that the forward portion 60a of the latch 60 has been inserted into the rearward end of the forward housing 20. The forward housing 20 and latch 60 are provided with cooperating engagement features 25, 65 to provide an automatic connection when brought together. In the illustrated embodiment, the engagement features comprise a cut-out 25 in the forward housing 20 and an outward projection 65 in the forward portion 60a of the latch 60. It may be noted that in the illustrated embodiment the rearward housing 30 extends over the cut out 25, thereby covering the opening in the housing and preventing the user from disengaging the projection 65 to force separation of the housing body portions 20 and 30.

Figure 4A:
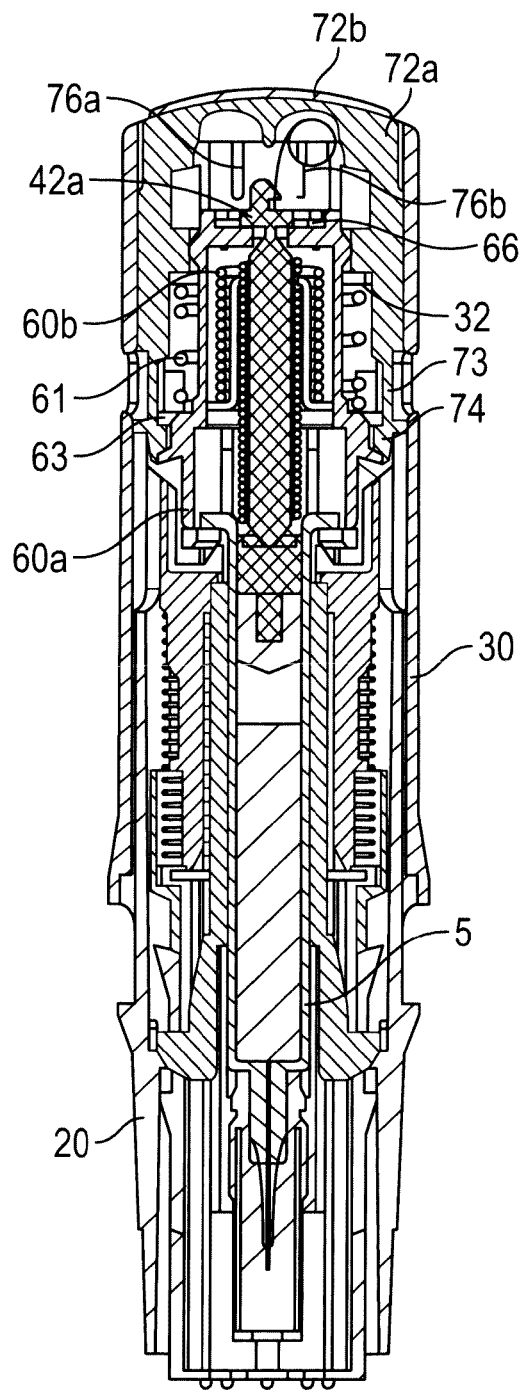
FIGS. 4A, 4B and 4C show two cross-sectional views and a detailed cross-section of the first embodiment in a pre-use configuration.

When assembled, the latch 60 is axially slidably connected to the rearward housing 30 via the trigger button 70. The rearward housing 30 includes a radial flange 32 which extends from the interior bore of the rearward housing 30. It will be noted that the radial flange 32 is spaced radially apart from the inner surface of the rearward housing wall along part of its circumference as shown in FIG. 4A (whereas in the cross section of 4B the flange includes connecting portions extending from the rearward housing). The resilient arms 73 of the trigger button 70 pass between the flange 32 and the inner side wall of the rearward housing 30 to engage the latch 60 (in other words the arms of the trigger button 70 pass over the flange 32 before engaging the latch 60). The forward ends of the resilient arms 73 are provided with inwardly projecting tabs which cooperate with corresponding outwardly projecting tabs 63 provided on a radially outer portion of the latch 60. It will be noted that both the tabs 63 and 74 have an angled profile such that the resilient arms 73 may disengage and be deflected outwardly to allow forward movement of the trigger button 70 relative to the latch 60 but prevent disengagement in the reverse direction.

Thus, it will be noted that an axially extending (and at least partially annular) space is defined between interior of the forwardly extending arms 73 of the trigger button 70 and the exterior of the rearward portion 60b of the latch member 60. The radially spaced portion of the flange 32 is captive within the space S. Also captive within the space is the housing biasing spring 61. The housing biasing spring 61 may, thus, act between a forward face of the flange 32 and a rearward face of the latch 60.

Figure 4B:
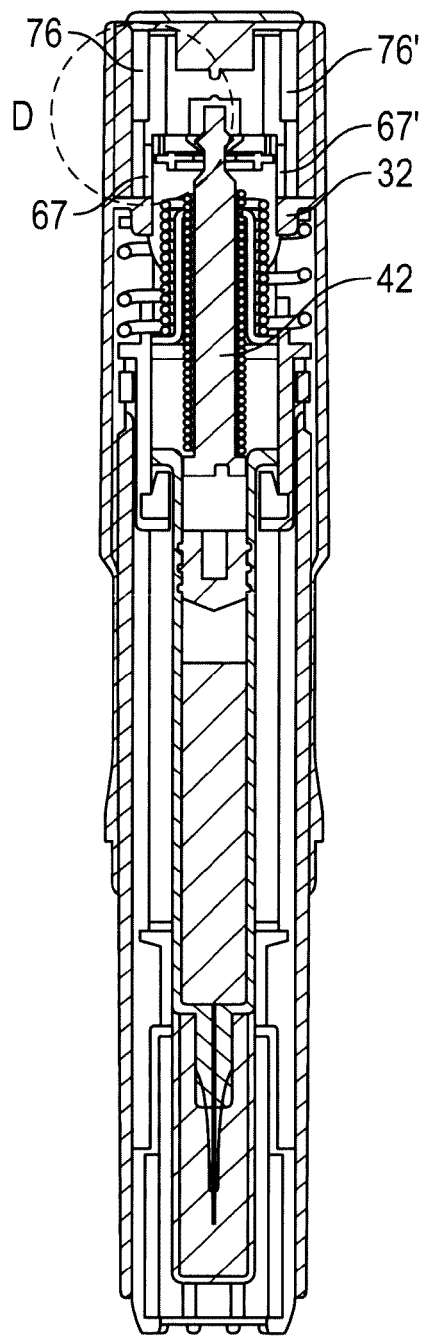

The operation of the latch and trigger arrangement will now be described with reference to FIGS. 4A and 4B which show a cross section view of the injector in a fully-assembled, pre-use configuration. The two cross-sections are viewed from planes extending through the longitudinal axis of the autoinjector and substantially perpendicular to one another. As the housing of the autoinjector 1 has a substantially oval or elliptical profile, it will be noted that FIG. 4A corresponds to a plane which is aligned with the major axis and FIG. 4B corresponds to a plane which is aligned with the minor axis.

Figure 4C:
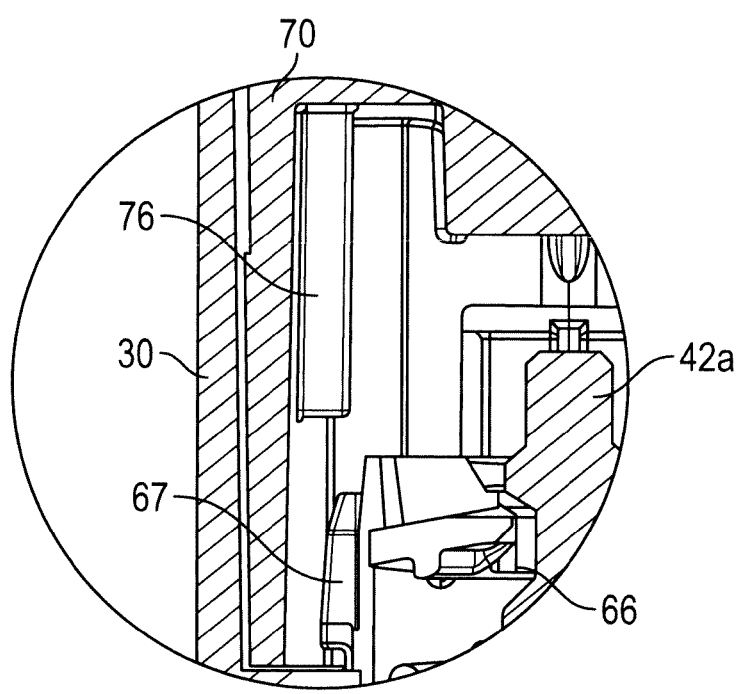

In FIG. 4, the forward and rearward sub-assemblies 2, 3 have been connected such that the housing fully encloses the syringe 5. This is the configuration in which the autoinjector may typically be provided to the end-user. The cap 10 has been removed from the front end of the forward body 20 of the housing. The rearward enlarged head 42a of the plunger is retained in the latch aperture 66 of the latch 60. To provide a reliable latching arrangement but which is also readily releasable in use, the ration of the cross sectional size of the reduced neck portion to the enlarged head may be between 25 and 75%. In particular a ration of around 50 to 60% may, for example, be particularly effective. The forward and rearward housings 20 and 30 are biased apart by the spring 61 and, as such, the trigger button 70 is rearward of the latch 60 (it will be appreciated that the trigger button may additionally be biased rearwardly). The sprung arms 73 of the trigger button 70 are engaging the tabs 63 of the latch 60.

In accordance with an embodiment of the invention the inner wall of the trigger button 70 is provided with two diametrically opposed pairs of axially aligned inwardly projecting ribs 76, 76'. Each pair of ribs 76, 76' consists of a pair of transversely spaced apart projections 76a and 76b. The ribs 76, 76' may have a tapered profile as they extend rearwardly (which it will be understood from the below description may provide a progressive engagement/action). In the initial, pre-use position of FIG. 4 the ribs 76, 76' are positioned rearwardly of the latch 60.

The latch 60 is provided with corresponding features for engaging the ribs 76, 76'. In the illustrated embodiment, the corresponding features comprise outwardly extending projections 67 which are formed on an outer surface of each resilient quadrant of the rearward portion of the latch 60b. As such, one outward projection 67 is provided on each quadrant and corresponds to one of the corresponding two pairs of ribs on the trigger button 70. The projections 67 extend forwardly along the outer wall of the resilient quadrant of the latch 60b and inwardly inclined as they extend forwardly. Thus, the projections 67 provide a cam surface along which the forward end of the respective rib 76 will run during forward movement of the trigger button 70 relative to the latch 60.

Figure 5A:
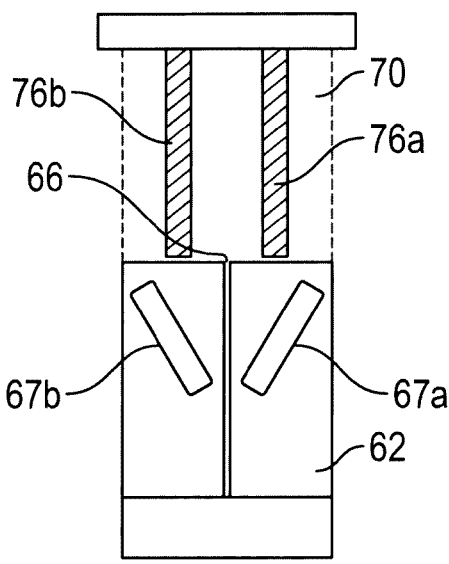
FIGS. 5A, 5B, and 5C show a schematic representation of the operation of the latch and trigger arrangement according to an embodiment.
Figure 5B:
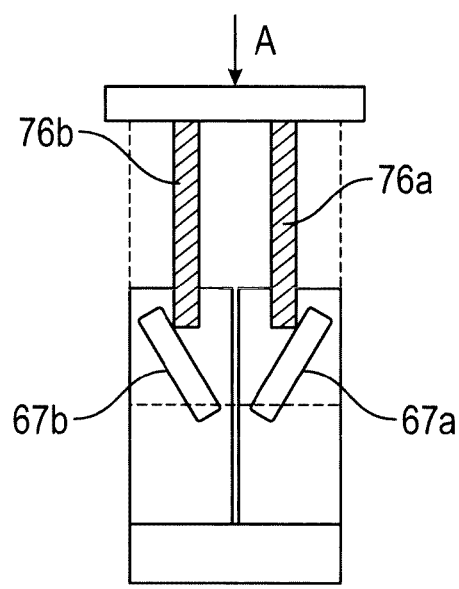
Figure 5C:
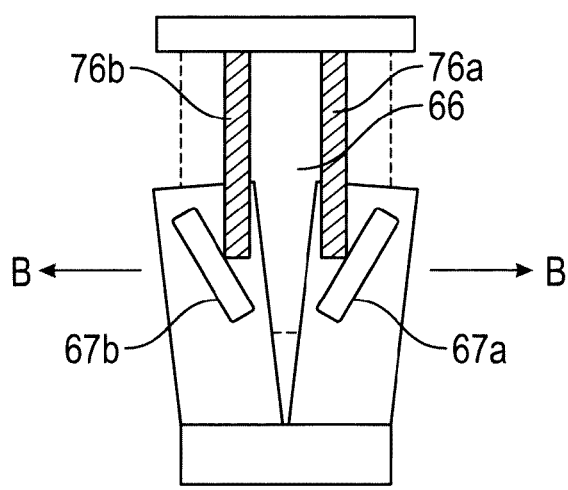

The camming action of the ribs 76 and projections 67 is illustrated schematically in FIG. 5 (in which features such as the plunger and housing are omitted for clarity). In FIG. 5A the trigger 70 is in the initial position and the ribs 76 are spaced axially apart from the camming surfaces defined by the projections 67 on the quadrants of the rear portion of the latch 62. The trigger 70 is urged forwardly in the direction of button A relative to the latch to bring the camming surfaces 76, 67 into engagement as shown in FIG. 5B. As the trigger 70 is urged further forward the ribs 76 travel along the surface of the projections 67. The ribs 76 are relatively rigid (due to being moulded into the side wall of the trigger 70) and the projections are fixed relative to the latch 62. Thus, the resulting force from the engagement of the camming features 76, 67 is to deflect the resilient segments of the rear portion 62b of the latch transversely away from one another in the direction shown by the arrows B of FIG. 5C. As a result the effective diameter of the latch aperture 66 is expanded (to release the head of the plunger)

It will of course be appreciated that whilst in the above embodiment ribs 76 are provided on the trigger 70 and angled projections 67 are provided on the latch, these features could be altered whilst still providing corresponding camming arrangements. For example, the features on the latch 60 could be straight and the features on the trigger could be angled. Further, one of the latch 60 and trigger 70 could be provided with a groove or recess into which a projection of the other is received (and in such an arrangement, a wall of the recess may provide a camming surface).

Figure 6A:
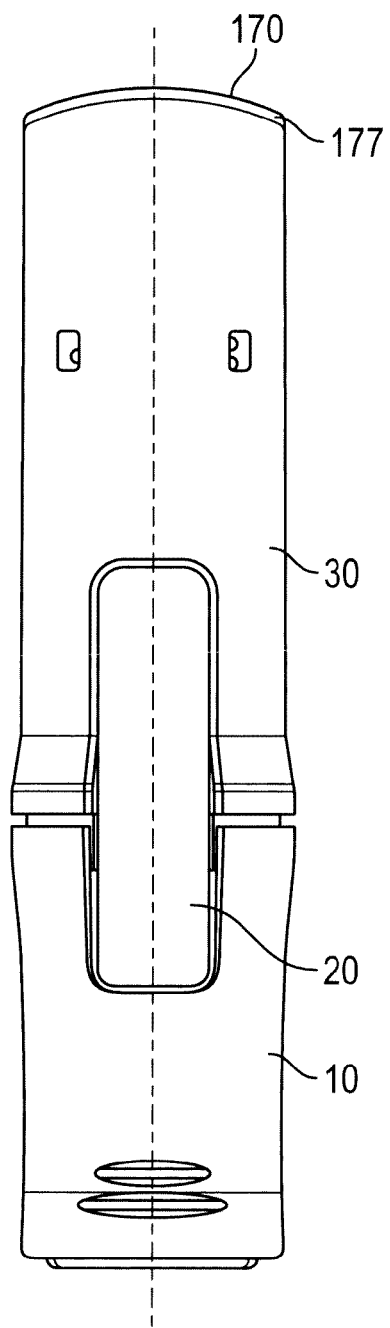
FIGS. 6A and 6B show an external view and cross-sectional view of an autoinjector according to a further embodiment of the invention.

Whilst the embodiment of FIGS. 1 to 4 includes a trigger in the form of an axially slidable button 70, an alternate embodiment is shown in FIG. 6 in which the button is replaced by a closure element 170 which is fixed relative to the rear housing 30. This provides a "pressure only" variant of the injection device in which the delivery mechanism 40 is released by pressing the device against an injection site and without the need for the user to depress a trigger button. In other words, the device is activated only by the relative sliding action between the front 20 and rear 30 body portions.

The forward assembly 2 and delivery mechanism of this embodiment is identical to the previous button activated embodiment and, therefore, provides a convenient method and system of manufacture in which either device may be produced using common manufacturing lines. The closure element 170 is similar in shape and construction to the trigger button 70 of the previous embodiment (which advantageously allows the rear housing 30 to be substantially the same, or even identical, to the rear housing of the button activated embodiment).

The closure 170 is arranged to be received in the end of the rearward housing 30 in a similar manned to the button 70. However, the rearward end of the element 170 is provided with a flange 177 which abuts the rearward end face 32 of the rearward housing 30 to fix the closure in a forward direction relative to the housing. Forward of the flange, cooperating features 33 and 173 are provided on an outer surface of the closure 170 and the inner surface of the rearward housing 30. At least one of the cooperating features 173 and 33 are provided with a barbed profile, to provide a snap fit arrangement, such that the closure 170 can be inserted forwardly into the housing 30 but is then fixed against rearward relative. Thus, once assembled the closure 170 is fixed in both a forward and rearward axial direction relative to the rearward housing 30.

Figure 6B:
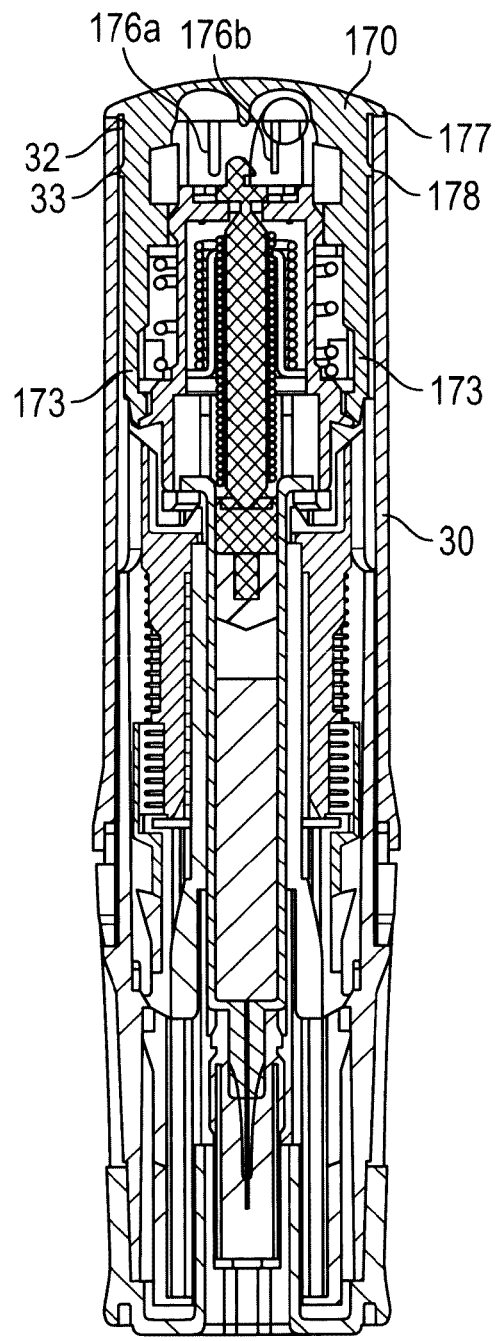

As seen best in the cross section of FIG. 6B, the closure element 170 includes sprung forwardly extending legs 173 which engage tabs of the latch 60 in an identical manner to those of legs 73 of the button 70. These legs 173, therefore, provide an engagement between the latch 60 (and therefore forward assembly 2) and the rearward assembly 3 and only allow for relative forward movement of the rearward housing 30.

It will be noted that the rearward portion of closure 170 provides the trigger arrangement in the form of axially extending ribs 176a and 176b (and a diametrically opposing pair of ribs). It will be appreciated that these ribs 176 are arranged to activate the device in exactly the same manner as those of the button 70.

For completeness, it may be noted that the distinction between the operation of the two embodiments is as follows. In the first embodiment, the rearward housing 30 initially slides forwardly (in response to the user holding the rear housing and pressing the front of the device against an injection site) with the trigger button 70 remaining fixed relative to the latch 60. The relative movement of the housing 30 moves an interlock arrangement out of alignment. This movement acts to reveal the button 70 at the rear of the rearward housing 30, then allows the button 70 to be urged forwardly to release the latch 60. In the second embodiment, the rearward housing 30 and closure 170 are urged forwardly together until the trigger features 176 come into engagement with the latch 60.

The skilled person will appreciate that when designing a device according to an embodiment of the invention the point of release of the latch 60 may be readily adjusted to provide the desired sequencing by adjusting the shape, profile and relative position of the camming surfaces 76/176 and 67 provided on the latch 60 and trigger 70. Further, the arrangement of embodiments of the invention may provide more precise control of the latch release than devices which rely upon either the forward biasing of the delivery mechanism on the plunger or contact with the plunger to release the latch. For example, the arrangement of the invention may be useful in ensuring that issues such as plastic creep do not prevent successful release of the plunger 42 from the latch 60 if the injector device has been stored for an extended period before use.

A further advantage of the arrangement of the invention is that by providing the engagement between the latch 60 and the trigger 76/176 at an outer surface of the latch 60 further clearance may be provided within the rear portion of the button 70 or closure 170 to improve operation of the indication arrangement 90.

Figure 7B:
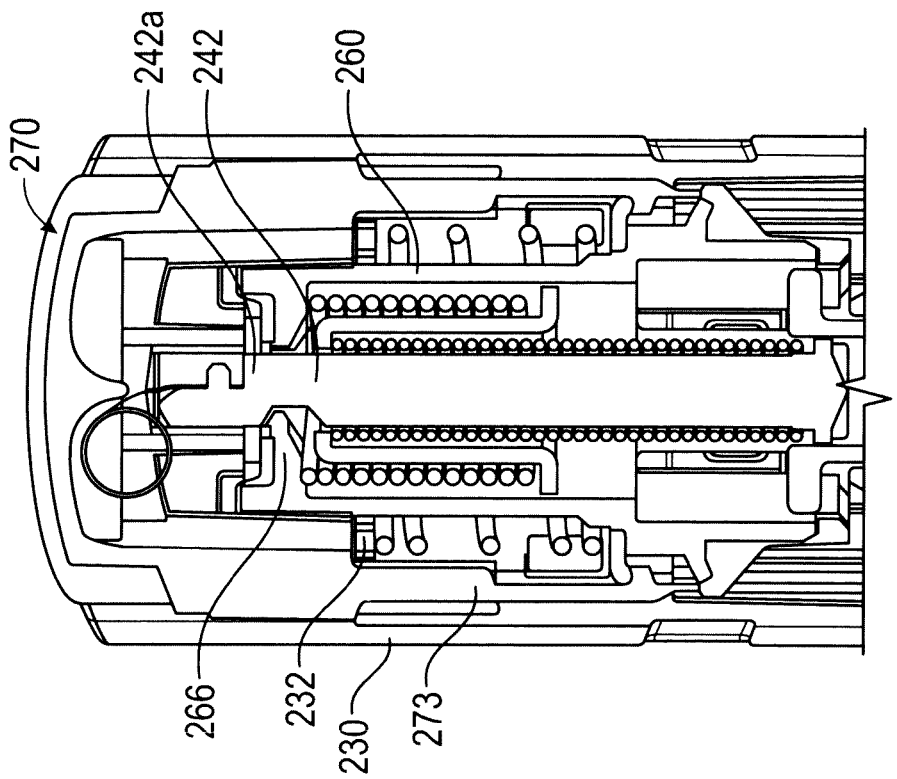
FIGS. 7A and 7B show detailed cross sectional views of an autoinjector according to a further embodiment of the invention in a pre-use configuration.
Figure 7A:
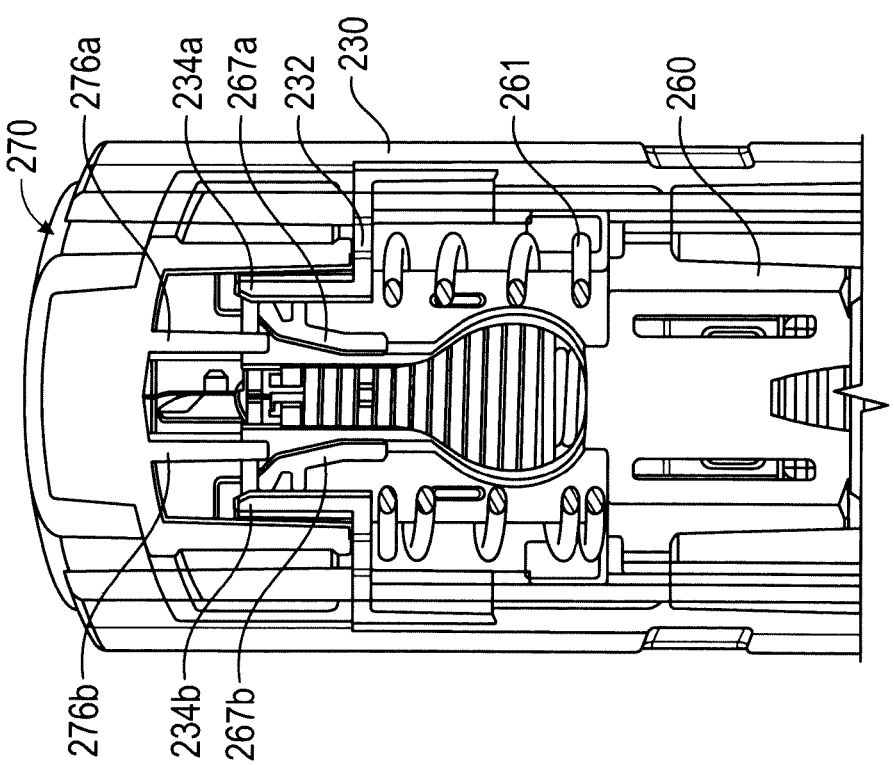
Figure 8B:
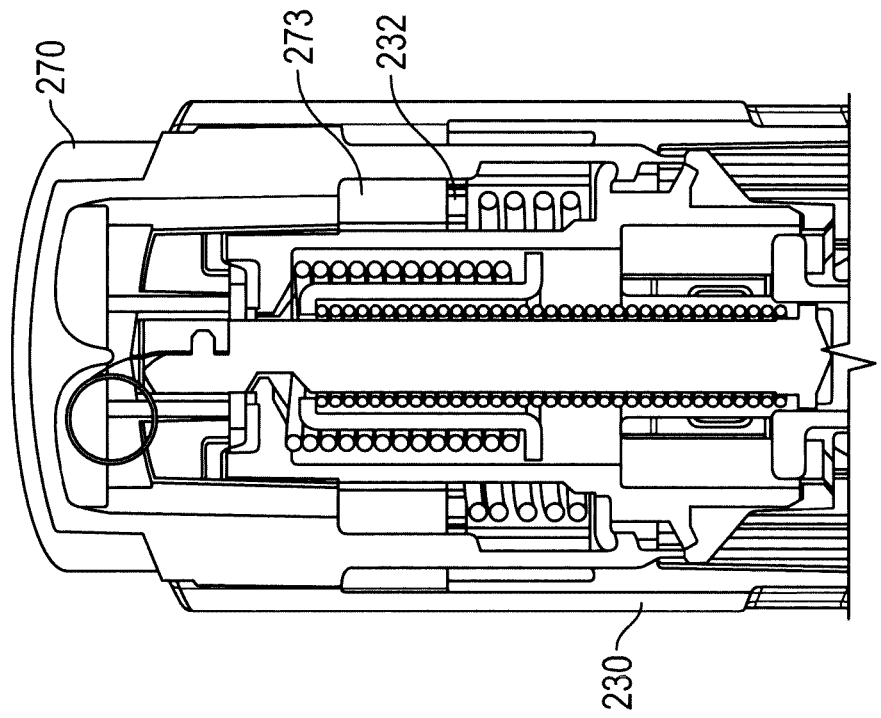
FIGS. 8A and 8B show detailed cross sectional views of the autoinjector of FIG. 7 in an intermediate configuration.
Figure 8A:
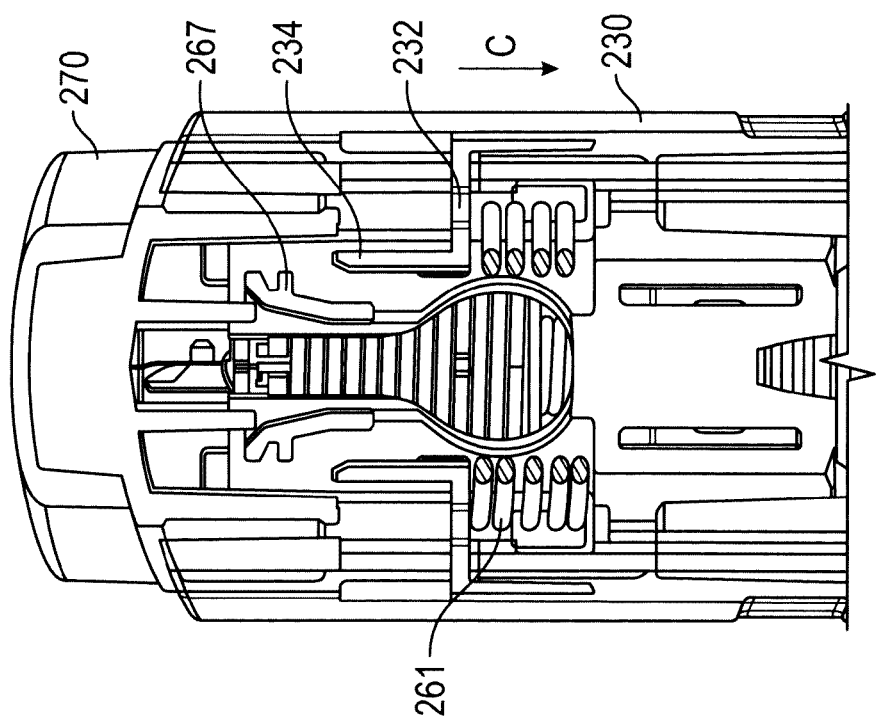
Figure 9B:
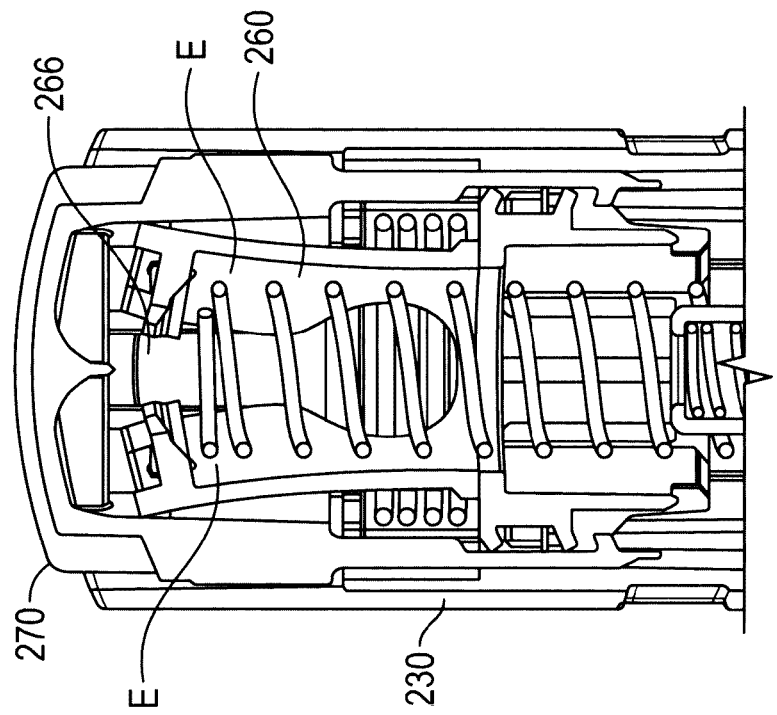
FIGS. 9A and 9B show detailed cross sectional views of the autoinjector of FIG. 7 in a fired configuration.
Figure 9A:
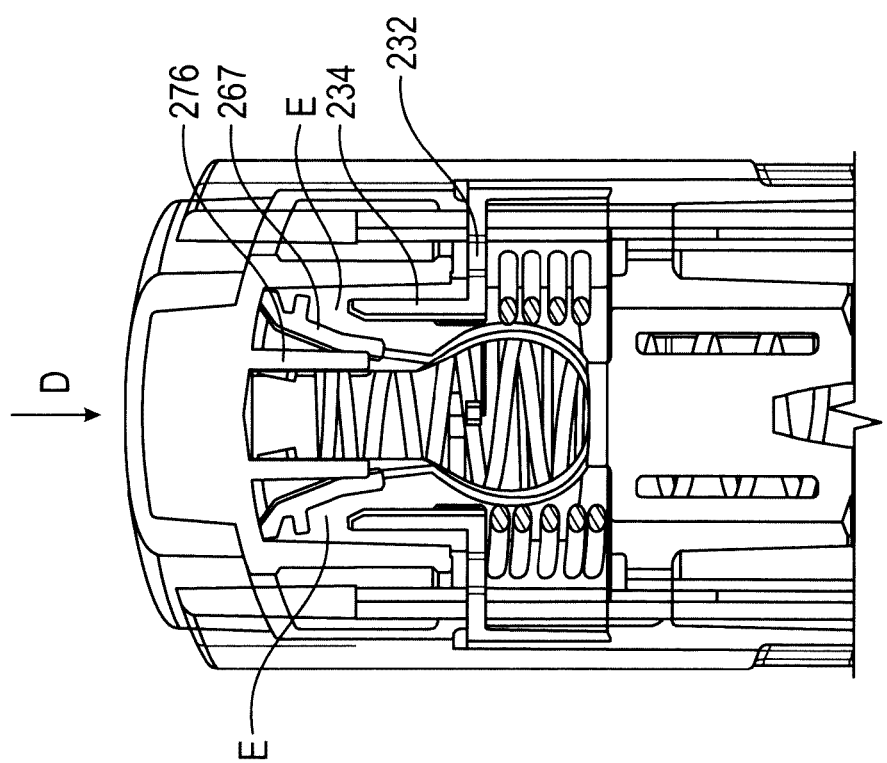

A further button activated embodiment of the invention is shown in sequential operation in FIGS. 7 to 9. Each of FIGS. 7 to 9 show two different cross sectional views through the same device. The operation of this embodiment is also illustrated schematically in FIG. 10. This embodiment has been modified to provide an arrangement which may provide a more resilient/robust latching of the plunger 242 against the drive mechanism (for example to improve resistance to accidental release in the event that the device is jarred such as by being dropped). As will be explained in further detail below, in particular the embodiment has been modified such that the rear body 230 may independently prevent release of the latch 260. Further the engagement between the latch 230 and plunger 242 has been modified to ensure that even when the rear body 230 has been moved the plunger 242 can be held by the latch 260 (i.e. without any support from the rear body 230).

The overall operation principle of the embodiment of FIGS. 7 to 10 is substantially the same as the button-activated embodiment of FIGS. 1 to 5. Initially, as shown in FIG. 7 (and schematically in FIG. 10A), the plunger 242 is retained within an aperture 266 at the rearward end of a latch 260. The latch 260 is fixed relative to a forward body portion (not shown) and the rearward body portion 230 is biased relatively rearwardly by a housing biasing spring 261 (which could also be referred to as an interlock spring). The spring 261 acts between a forward surface of a flange 232 and a rearward surface associated with the latch 260. The flange 232 (and an outer portion of the housing 230) initially abuts a forward part of the trigger button 270 (typically a part of the forwardly extending arms 273). Thus, in the initial configuration of FIG. 7 it is not possible to move the button 270 forward to activate the device. In other words, the interaction between the trigger button 270 and rearward housing 230 (under the influence of the spring 261) is providing an interlock to prevent triggering of the device.

In the embodiment of FIG. 7 the rearward housing 230 is further provided with a blocking arrangement in the form of ribs 234a, 234b which directly restrict the expansion of the latch 260. The ribs 234 extend from the flange 232 in the interior of the housing 230. The ribs 234a and 234b are each positioned immediately outside of one of the pair of the outwardly extending projections 267a, 267b. It will be appreciated that such a pair of ribs 234 may be provided on either side of the housing 230 to provide a blocking arrangement for each of a set of projections 267 provided on radially opposing sides of the latch 260. It may be noted that the projection 267 in this embodiment have been formed with an "f" shaped profile with an additional lateral member to provide an additional abutment/engagement feature with the ribs 234.

During use, a user offers the device up to an injection site and urges the device into firm contact whilst gripping an outer surface of the rearward body housing 230. This causes the rearward housing to slide forward relative to the latch 260 (and associated forward housing) in the direction of arrow C. This, movement compresses the spring 261 and moves the device into the configuration of FIGS. 8 (and 10B). In this position the rearward end of the trigger button 270 is exposed (providing a visual indication that the device is ready to fire) and the interlock features of the body 230 are moved forwardly clear of the corresponding internal features of the trigger 270. It will further be noted that the ribs 234 are moved forward with the rearward body 230 and out of blocking alignment with the projections 267 of the latch 260.

Figure 10A:
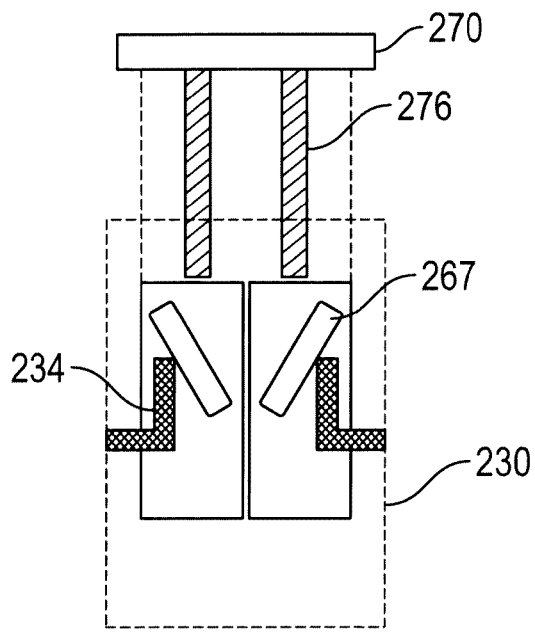
FIGS. 10A, 10B, 10C and 10D show a schematic representation of the operation of the latch and trigger arrangement according to the embodiment of FIG. 7.
Figure 10B:
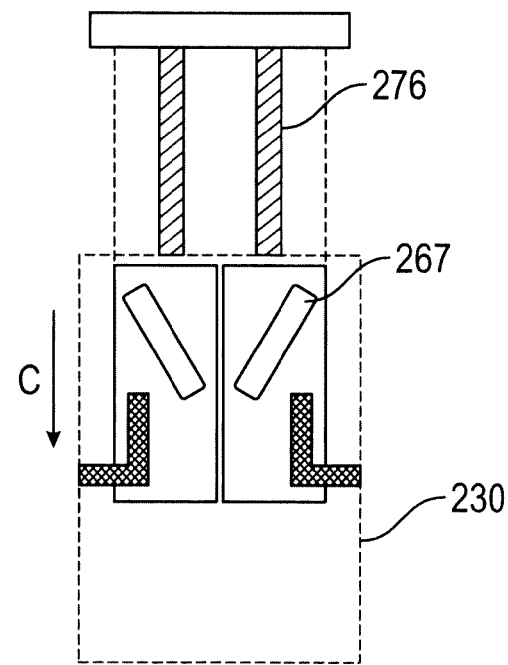
Figure 10C:
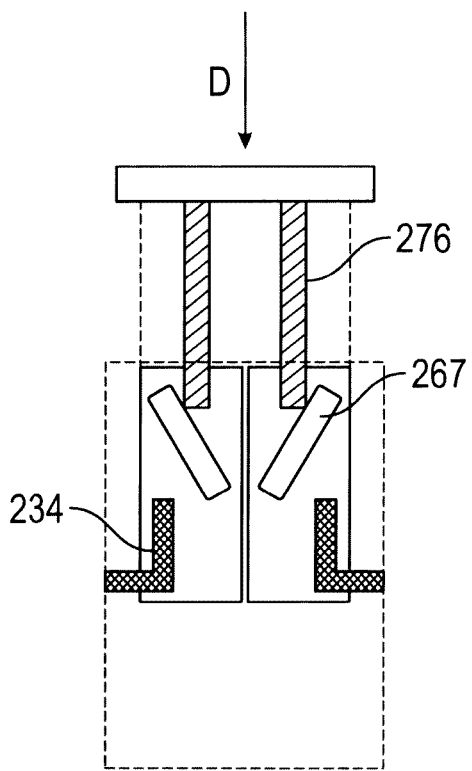
Figure 10D:
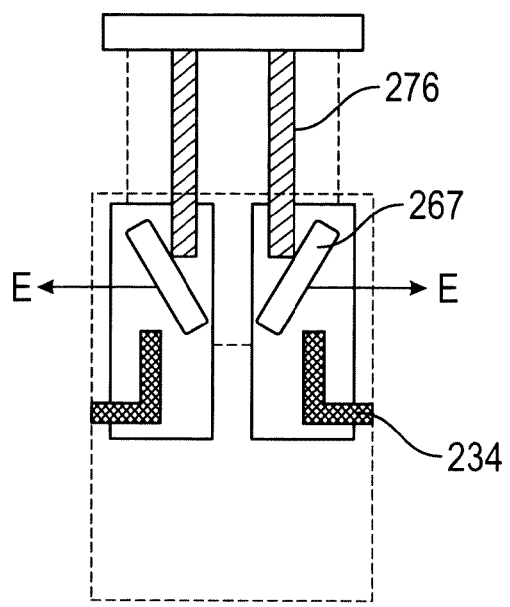

The user is subsequently able to urge the trigger button 270 forward in the direction of arrow D as shown in FIG. 9 and (schematically in FIGS. 10C and 10D). The movement of the trigger button forces the ribs 276 on the interior of the trigger 270 into the angled inwardly inclined surface on the interior of the projections 267. Thus, the latch 260 is subjected to a force which separates the segments in a transverse direction as shown by arrow E. Thus, the aperture 266 is expanded to release the head 242b of the plunger 240 and allow forward movement under the influence of the drive mechanism.

If the trigger and interlock are not activated in the correct sequence, for example due to a user attempting to press the trigger button 270 without having first pressed the device firmly against an injection site or if the device is dropped, the ribs 276 of the trigger 270 will force the projections against the ribs 234 of the blocking arrangement of the rearward housing 230. Thus, the system will effectively "bind" together and lock the latch 260 against accidental or premature release.

Figure 11A:
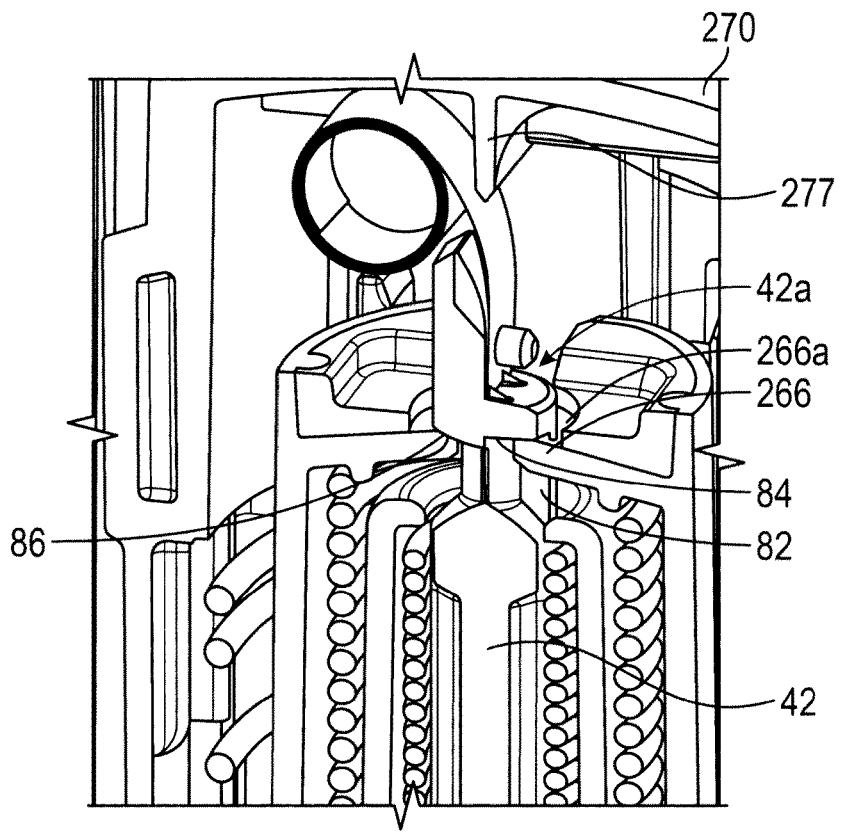
FIGS. 11A and 11B show a plunger arrangement for use in embodiments of the invention.
Figure 11B:
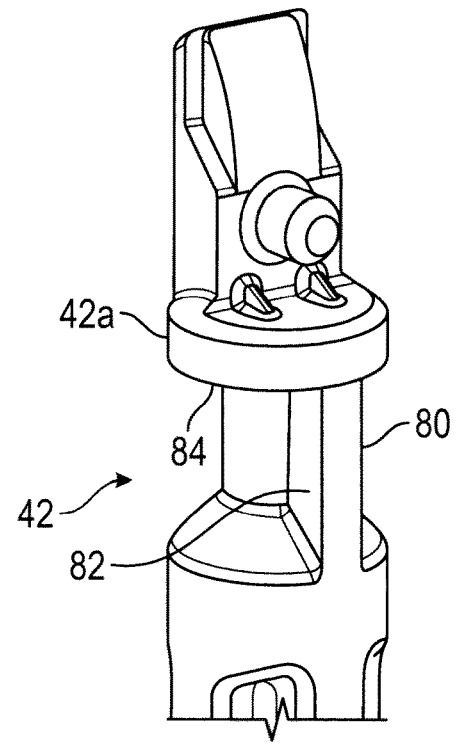

The plunger arrangement of the device of FIGS. 7 to 9 is shown in further detail in FIG. 11. The head of the plunger 242a is provided with an attachment for a coil spring 90 (which may be a constant force or "clock") to provide an end of dosage indication; however, other arrangements of the head may be used depending upon the requirements of the particular device. Between the main body of the plunger 242 and the head 242a is provided a reduced cross section neck 80. The neck 80 is sized and dimensioned to be received and retained in the aperture 266 of the latch 260 when the autoinjector is in a pre-use configuration (for example by having a width between 50 to 60% of the width of the head). Prior to release, the forward facing surface of the head 42a is retained against the rearward facing surface surrounding the aperture 266 of the latch 260.

The plunger arrangement of this embodiment also includes additional features to further reduce the risk of unintended or premature release of the head 42a from the aperture 266 of the latch 260 (and resulting accidental firing of the autoinjection device).

Firstly, the forward facing surface of the head 42a is provided with an asymmetric profile. More specifically, the forward facing surface is formed by a first segment 86 having a forward face which is angled forwardly at a first angle and a second segment 84 which is inclined at a shallower angle. The first 84 and second 86 segments may be on opposing radial sides of the plunger 42 and may engage different segments of the latch 260. The second segment 84 may be substantially radially aligned and extend substantially perpendicularly to the longitudinal axis of the plunger 42. The asymmetric profile of the forward face ensures that the surfaces cannot act together to urge the segments of the latch 260 radially apart (particularly once the rear body housing 130 has been moved forward to unlock the interlock so is no longer preventing movement of the latch 60). Thus, the arrangement of the head ensures that the plunger head 42a can only be released from the aperture 266 of the latch 260 by the trigger button 270 forcing the flexure of the segments of the latch 260 (even after the interlock has been disengaged).

The applicants have for example found that the facing surfaces of the interface could be angled between 0 and 45% facing angle. For example a 30 degree angle may be used (with the asymmetric face shape having at least one section with a different angle).

Advantageously, the shallow angle interface between the latch 260 and second segment 84 provides an increased friction engagement between the plunger head 42a and the latch 260. In contrast to an arrangement, such as that of the preceding embodiment, having a uniform tapered transition surface extending from the reduced diameter neck 80 to the head 42a, the interaction between the surface 84 of the head 42a and latch 260 urge the latch towards its closed position rather than act to splay the latch open. The asymmetric profile also provides a more reliable latching between the plunger 42 and latch 260 since the head 42a is retained on a known side of the latch.

In order to assist with reliably firing of the device the button 270 may be provided with an alignment member in the form of a central projection 277 on a forward facing surface which is arranged to ensure that the plunger 42 retains the correct alignment (i.e. centred) during firing. In particular, the projection 277 is positioned such that it is on the same side of the rearward most part of the plunger head 42a as the shallow angled segment 84. Thus, the projection 277 ensures that there is no risk of the plunger 42 remaining hung on the higher friction engagement segment.

Further, the aperture 66 and neck 80 of the plunger 42 are provided with complimentary non-rotational features which act to prevent relative rotation between the latch 260 and the plunger 42. The neck of the plunger 80 may be provided with a keyed profile which matches a corresponding profile of the aperture 266. For example, as shown in FIG. 11 the neck may be provided with a radial rib 82 and the aperture 266 may be provided with a correspondingly dimensioned slot 266a. The provision of non-rotation features may ensure that the device operates as intended even when the device has been subject to a drop or jar which might otherwise cause misalignment. In particular the applicants have identified that the non-rotation feature may for example, help to ensure correct operation of the coil spring end of dose indicator 90.

Although the invention has been described above with reference to preferred embodiments, it will be appreciated that various changes or modifications may be made without departing from the scope of the invention as defined in the appended claims.

For example, in either embodiment of the invention, the button 70, rear housing 30 or closure 170 may also be provided with features which block outward movement of the resilient portion 60b of the latch in an initial position. Thus, premature or accidental release of the delivery mechanism may be prevented and correct sequencing further ensured.

The invention claimed is:

1. A method of modular manufacture of an injector device comprising:
   providing a common forward body assembly;
   providing a common delivery mechanism assembly;
   providing two alternate rear body assembly types,
      wherein a first of the rear body assemblies is provided with a first trigger moveable relative to a rear housing of the first rear body assembly,
      wherein a second of the rear body assemblies is provided with a second trigger fixed relative to a rear housing of the second rear body assembly, and
      wherein the first trigger and the second trigger comprise sprung forwardly extending legs;
   selecting the first or the second rear body assembly; and
   assembling the common forward body assembly, the common delivery mechanism assembly, and the selected first or second rear body assembly about a syringe containing a medicament.

2. A method as claimed in claim 1, wherein both rear body assemblies are arranged to be connected to the common forward body assembly by slideable engagement.

3. A method as claimed in claim 1, wherein the trigger is engaged with the first rear body assembly or the second rear body assembly by a snap fit arrangement.

4. A method as claimed in claim 1, wherein the common delivery mechanism assembly includes a latch which is fixed relative to the common forward body assembly.

5. A method as claimed in claim 1, wherein the common delivery mechanism assembly includes a plunger, one or more drive springs for urging the plunger forward, and a latch.

6. A method as claimed in claim 5, wherein the sprung forwardly extending legs of the selected first or second rear body assembly engage with the latch of the common delivery mechanism assembly to retain the latch in a rearward position, and
   wherein, upon forward movement of the trigger relative to the common forward body assembly, the sprung forwardly extending legs release the latch and allow the one or more drive springs to move the plunger through the common forward body assembly to expel medicament from the syringe.

7. A method as claimed in claim 1, wherein the first of the rear body assemblies provides a button activated injection, and the second of the rear body assemblies provides a pressure activated injection device.

* * * * *